United States Patent [19]
Felmlee et al.

[11] Patent Number: 6,037,774
[45] Date of Patent: Mar. 14, 2000

[54] INERTIAL DRIVER DEVICE FOR MR ELASTOGRAPHY

[75] Inventors: Joel P. Felmlee; Richard L. Ehman, both of Rochester, Minn.

[73] Assignee: Mayo Foundation for Medical Education and Research, Rochester, Minn.

[21] Appl. No.: 09/057,405

[22] Filed: Apr. 8, 1998

Related U.S. Application Data

[60] Continuation-in-part of application No. 08/719,605, Sep. 25, 1996, Pat. No. 5,977,770, which is a division of application No. 08/325,834, Oct. 19, 1994, Pat. No. 5,592,085.

[51] Int. Cl.[7] .................................................... G01V 3/00
[52] U.S. Cl. ......................... 324/318; 324/318; 324/309; 600/438; 600/437
[58] Field of Search ..................................... 324/309, 318; 600/438, 437, 587, 424

[56] References Cited

U.S. PATENT DOCUMENTS

| | | | |
|---|---|---|---|
| 4,543,959 | 10/1985 | Sepponen | 324/309 |
| 5,131,392 | 7/1992 | Jolesz et al. | 324/309 |

*Primary Examiner*—Christine Oda
*Assistant Examiner*—Brij B. Shrivastav
*Attorney, Agent, or Firm*—Quarles & Brady LLP

[57] ABSTRACT

Devices for producing an oscillatory shear stress within an object positioned in a polarizing magnetic field of an NMR imaging system are used to perform MR elastography. In one embodiment shear stress is produced within the brain by vibrating the entire skull with a transducer that is gripped by the patient's teeth.

5 Claims, 4 Drawing Sheets

INERTIAL DRIVER DEVICE FOR MR ELASTOGRAPHY

This application is a continuation-in-part of application Ser. No. 08/719,605 filed Sept. 25, 1996, now U.S. Pat. No. 5,977,770, which is a division of application Ser. No. 08/325,834 filed Oct. 19, 1994, now U.S. Pat. No. 5,592,085.

STATEMENT REGARDING FEDERALLY SPONSORED RESEARCH

Not applicable

BACKGROUND OF THE INVENTION

The field of the invention is nuclear magnetic resonance imaging methods and systems. More particularly, the invention relates to devices for implementing MR elastography.

The physician has many diagnostic tools at his or her disposal which enable detection and localization of diseased tissues. These include x-ray systems that measure and produce images indicative of the x-ray attenuation of the tissues and ultrasound systems that detect and produce images indicative of tissue echogenicity and the boundaries between structures of differing acoustic properties. Nuclear medicine produces images indicative of those tissues which absorb tracers injected into the patient, as do PET scanners and SPECT scanners. And finally, magnetic resonance imaging ("MRI") systems produce images indicative of the magnetic properties of tissues. It is fortuitous that many diseased tissues are detected by the physical properties measured by these imaging modalities, but it should not be surprising that many diseases go undetected.

Historically, one of the physician's most valuable diagnostic tools is palpation. By palpating the patient a physician can feel differences in the compliance of tissues and detect the presence of tumors and other tissue abnormalities. Unfortunately, this valuable diagnostic tool is limited to those tissues and organs which the physician can feel, and many diseased internal organs go undiagnosed unless the disease happens to be detectable by one of the above imaging modalities. Tumors (e.g. of the liver) that are undetected by existing imaging modalities and cannot be reached for palpation through the patient's skin and musculature, are often detected by surgeons by direct palpation of the exposed organs at the time of surgery. Palpation is the most common means of detecting tumors of the prostate gland and the breast, but unfortunately, deeper portions of these structures are not accessible for such evaluation. An imaging system that extends the physician's ability to detect differences in tissue compliance throughout a patient's body would extend this valuable diagnostic tool.

Any nucleus which possesses a magnetic moment attempts to align itself with the direction of the magnetic field in which it is located. In doing so, however, the nucleus precesses around this direction at a characteristic angular frequency (Larmor frequency) which is dependent on the strength of the magnetic field and on the properties of the specific nuclear species (the magnetogyric constant γ of the nucleus). Nuclei which exhibit this phenomena are referred to herein as "spins", and materials which contain such nuclei are referred to herein as "gyromagnetic".

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. A net magnetic moment $M_z$, is produced in the direction of the polarizing field, but the randomly oriented magnetic components in the perpendicular, or transverse, plane (x-y plane) cancel one another. If, however, the substance, or tissue, is subjected to a magnetic field (excitation field $B_1$) which is in the x-y plane and which is near the Larmor frequency, the net aligned moment, Mz, may be rotated, or "tipped", into the x-y plane to produce a net transverse magnetic moment $M_t$, which is rotating, or spinning, in the xy plane at the Larmor frequency. The practical value of this phenomenon resides in the signal which is emitted by the excited spins after the excitation signal $B_1$ is terminated. There are a wide variety of measurement sequences in which this nuclear magnetic resonance ("NMR") phenomena is exploited.

When utilizing NMR to produce images, a technique is employed to obtain NMR signals from specific locations in the subject. Typically, the region which is to be imaged (region of interest) is scanned by a sequence of NMR measurement cycles which vary according to the particular localization method being used. The resulting set of received NMR signals are digitized and processed to reconstruct the image using one of many well known reconstruction techniques. To perform such a scan, it is, of course, necessary to elicit NMR signals from specific locations in the subject. This is accomplished by employing magnetic fields ($G_x$, $G_y$, and $G_z$) which are superimposed on the polarizing field $B_0$, but which have a gradient along the respective x, y and z axes. By controlling the strength of these gradients during each NMR cycle, the spatial distribution of spin excitation can be controlled and the location of the resulting NMR signals can be identified.

It is well known that NMR can be used to detect and image the movement of spins. As disclosed in U.S. Pat. No. Re. 32,701 entitled "NMR Scanner With Motion Zeugmatography", acquired NMR signals can be sensitized to detect moving spins by applying a bipolar magnetic field gradient at the proper moment in each NMR measurement sequence. The phase of the resulting NMR signal measures the velocity of spins along the direction of the motion sensitizing magnetic field gradient. With more complex motion sensitizing magnetic field gradients, higher orders of motion, such as acceleration and jerk can also be measured with this method.

It has been found that MRI imaging can be enhanced when an oscillating stress is applied to the object being imaged in a method called MR elastography. The method requires that the oscillating stress produce shear waves that propagate through the organ, or tissues to be imaged. These shear waves alter the phase of the NMR signals, and from this the mechanical properties of the subject can be determined. In many applications, the production of shear waves in the tissues is merely a matter of physically vibrating the surface of the subject with an electromechanical device such as that disclosed in above-cited U.S. Pat. No. 5,592,085. For example, shear waves may be produced in the breast and prostate by direct contact with the oscillatory device. Also, with organs like the liver, the oscillatory force can be directly applied by means of an applicator that is inserted into the organ.

Certain tissues and organs cannot be directly driven to produce the shear waves required for elastography. For example, shear waves cannot be directly coupled through the skull to the brain. In this case the skull represents a shear wave barrier, which encloses the organ of interest. Another example is the spinal cord which is substantially enclosed by the vertebrae. In each case, the shear waves cannot be directly transmitted to the organ of interest.

SUMMARY OF THE INVENTION

The present invention relates to the imaging of mechanical characteristics of a subject, and more particularly, to a device for applying an oscillatory movement to a subject positioned in the polarizing magnetic field of an NMR imaging system in order to establish mechanical waves therein which enable MR elastography to be practiced.

The oscillatory movement of the subject produces inertial forces therein, and these forces acting in combination with substantially rigid boundaries around the subject form mechanical waves in the subject that enable its mechanical properties to be assessed using MR elastography.

A general object of the invention is to establish mechanical waves in a subject that enable its mechanical properties to be assessed using elastography. It has been discovered that MR elastography can be successfully practiced when shear waves are indirectly produced in the subject.

A more specific object of the invention is to image the mechanical properties of the brain using MR elastography. By shaking the entire head of a subject, inertial forces are produced throughout the brain to generate mechanical waves that reveal through MR elastography the mechanical properties throughout the brain.

The foregoing and other objects and advantages of the invention will appear from the following description. In the description, reference is made to the accompanying drawings which form a part hereof, and in which there is shown by way of illustration, preferred embodiments of the invention. Such embodiments do not necessarily represent the full scope of the invention, however, and reference is made therefore to the claims herein for interpreting the scope of the invention.

GENERAL DESCRIPTION OF THE INVENTION

Figure 1:
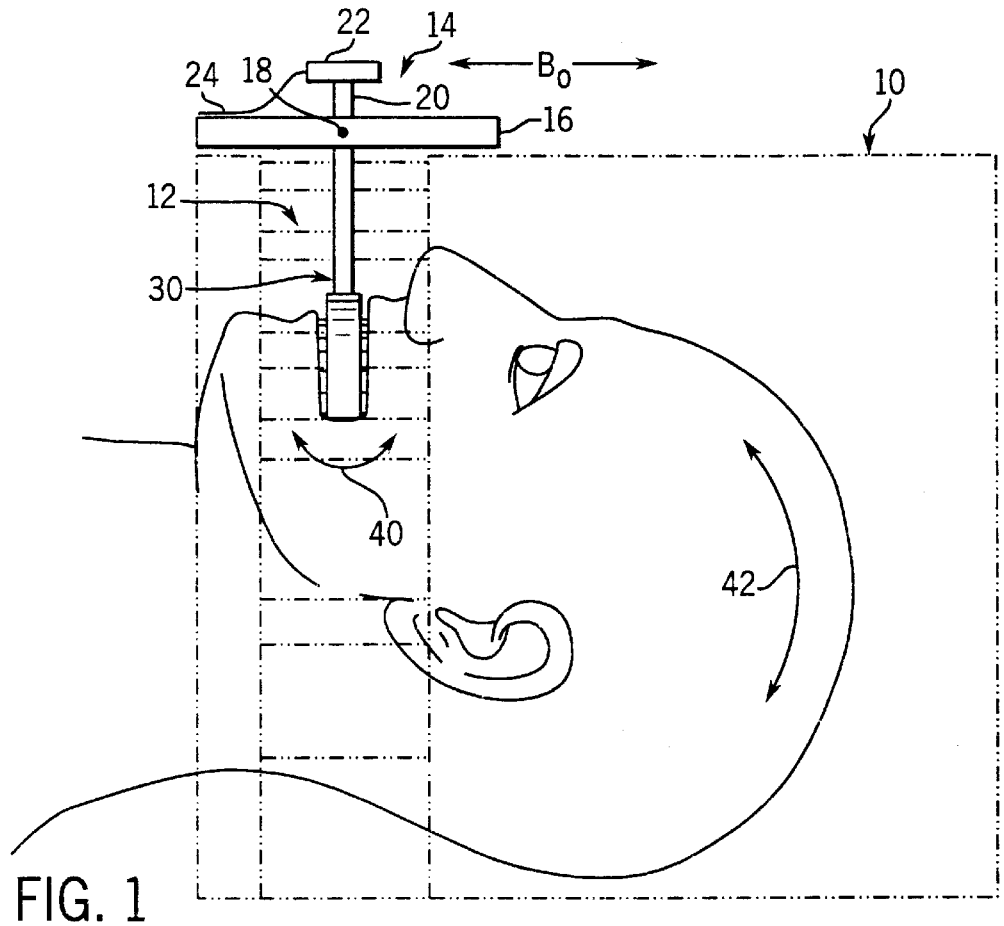
FIG. 1 is an elevation view of a preferred embodiment of the transducer that is used to practice the present invention for imaging the brain.

The physical properties of tissue are measured using MR elastography by applying a stress (e.g. tension, pressure, or shear) and observing the resulting strain (e.g. elongation, compression, rotation). By measuring the resulting strain, elastic properties of the tissue such as Young's modulus, Poisson's ratio, the shear modulus, and the bulk modulus, can be calculated. By applying the stress in all three dimensions and measuring the resulting strain, the elastic properties of the tissue can be completely defined.

By observing the rate at which the strain decreases as a function of distance from the stress producing source, the attenuation of the strain wave can be estimated. From this, the viscous properties of the gyromagnetic medium may be estimated. The dispersion characteristics of the medium can be estimated by observing the speed and attenuation of the strain waves as a function of their frequency. Dispersion is potentially a very important parameter for characterizing tissues in medical imaging applications.

The present invention is employed in a system such as that described in the above-cited U.S. Pat. No. 5,592,085 which provides a means for measuring the strain in gyromagnetic materials such as tissues using NMR methods and apparatus. The Larmor equation is given by $$\omega = \gamma \overline{B} \tag{1}$$

where $\omega$ is the angular resonant frequency of the NMR signal produced by spins having a characteristic gyromagnetic ratio of $\gamma$ when placed in a magnetic field having a density and direction $\overline{B}$. The magnetic field vector $\overline{B}$ can be broken down into two components $$\overline{B} = \overline{B}_0 + r\overline{G}_r \tag{2}$$

where $B_0$, is the polarizing magnetic field, r is the location of the spins, and $G_r$ is the magnetic field gradient.

Since the angular frequency of the NMR signals produced by the spins is the rate of change of their phase, the phase of the spin signals as a function of time is as follows:

$$\phi(t) = \int \omega(t) dt. \tag{3}$$

Substituting equation (1), the relationship between NMR signal phase and the applied gradient field is obtained $$\phi(t) = \gamma \int G(t') r(t') dt', \tag{4}$$

where G and r are expressed as functions of time (t') for obtaining a general expression of the Larmor equation. This equation indicates that the NMR signal produced by moving spins will accrue a phase shift relative to that accrued by static spins when in the presence of a magnetic field gradient.

If an oscillating stress is applied to tissue along the direction r at an angular frequency $\omega_p$, a wave is launched and spins are displaced by amounts determined by the elastic properties of the tissue. If it is assumed that this propagation occurs without loss, the displacement ($\Delta$) of spins at location (r) may be expressed as follows:

$$\Delta = \Delta_0 \cos(\omega_p t + kr + \theta), \tag{5}$$

where $\Delta_0$ is the maximum displacement produced by the applied stress, k is the wave number, and $\theta$ is the phase offset of the spin displacement relative to the applied oscillating stress. The wave number k is equal to $2\pi$ radians divided by the wavelength ($\lambda$) of the propagated wave, and if it is assumed that the spin displacement occurs for just one cycle (t=0 to T) of the applied oscillating stress, then the NMR signal produced by the spin will accumulate a phase indicated by the following expression:

$$\phi(t) = \Upsilon \int_{t=0}^{t=T} G(t') \Delta_0 \cos(\omega_p t + kr + \theta) \, dt' \tag{6}$$

If the magnetic field gradient G(t') is constant during this time period, no phase signal will be accumulated. However, if the magnetic field gradient G(t') is synchronized with the applied stress and is switched in polarity half way through the time period (T), the phase of the NMR signal (φ) at the completion of the time period will be proportional to the displacement of the spins. This displacement along the r direction is the strain which results from the applied stress along the same direction r.

NMR measurements can be made with imaging gradients applied, and a strain image indicative of the longitudinal strain at each pixel may be reconstructed. This strain image has pixel values as follows:

$$S_L(t, r) = \Delta_0 \cos(\omega_p t + kr). \quad (7)$$

If the measurement is repeated with the oscillating stress in the same direction, but with the alternating gradient G(t') oriented along each of the orthogonal axes, the displacements, along these axes can be determined and the orthogonal strain ($S_T$) calculated.

From this information Poisson's ratio (σ) can be calculated as follows:

$$\sigma = S_T/S_L \quad (8)$$

Further information can be learned about the elastic properties of tissues by changing the phase relationship of the applied oscillatory stress and the synchronized alternating motion gradient. For example, if the phases are offset π/2 radians, a second strain image $S_0$ is produced having the following pixel values:

$$S_0(t, r) = \Delta_0 \cos(\omega_p t + kr + \pi/2) \quad (9)$$
$$= \Delta_0 \sin(\omega_p t + kr)$$

The gradient in each of the strain images $S_L$, and $S_0$ may be defined as follows:

$$\nabla S_L = \frac{\partial S_L}{\partial x}\vec{i} + \frac{\partial S_L}{\partial y}\vec{j} \quad (10)$$
$$\nabla S_0 = \frac{\partial S_0}{\partial x}\vec{i} + \frac{\partial S_0}{\partial y}\vec{j}$$

Using these gradients, the wave number (k) of the propagated wave at each image pixel can be calculated as follows:

$$k = \sqrt{|\nabla S_L|\cdot|\nabla S_L| + |\nabla S_0|\cdot|\nabla S_0|} \bigg/ \sqrt{S_0^2 + S_L^2} \quad (11)$$

Knowing the frequency (f) of the applied oscillatory stress, the propagation velocity (c) can then be calculated at each image pixel as long as the viscosity effects are not significant.

$$\lambda = 2\pi/k$$

$$c = f\lambda$$

If the density (ρ) of the gyromagnetic medium is known, the propagation velocity (c) can be used to calculate Young's modulus (Y):

$$Y = c^2 \rho. \quad (12)$$

Since compliance is the inverse of Young's modulus (i.e. 1/Y), the compliance of the gyromagnetic medium may also be calculated. An image in which pixel intensity is determined by the calculated compliance has diagnostic value in medicine because such an image displays what a physician feels when manually palpating tissue. With the knowledge of Poisson's ratio (σ) and the Young's modulus (Y) all other values of moduli, namely the shear modulus (μ) and the bulk modulus (β) may be calculated, since only two of these four elastic properties are actually independent. Bulk modulus (β) can be expressed from Young's modulus and Poissons ratio, in the following way:

$$Y = 3\beta(1 - 2\sigma).$$

Shear Modulus (μ) can be expressed as follows:

$$Y = 2\mu(1 + \sigma).$$

It should be apparent that the oscillatory stress may be applied in three orthogonal directions and the synchronized gradient field may also be applied in three separate orthogonal directions for each applied stress direction. Spin displacements (Δ, η, Σ) in all three directions may be measured, and all the components of the strain dyadic (second-rank tensor field), given in the following matrix may be measured:

$$\begin{pmatrix} \frac{\partial \Delta}{\partial x} & \frac{\partial \eta}{\partial x} & \frac{\partial \Sigma}{\partial x} \\ \frac{\partial \Delta}{\partial y} & \frac{\partial \eta}{\partial y} & \frac{\partial \Sigma}{\partial y} \\ \frac{\partial \Delta}{\partial z} & \frac{\partial \eta}{\partial z} & \frac{\partial \Sigma}{\partial z} \end{pmatrix}$$

With these measurements it is possible to characterize all the elastic properties of the gyromagnetic medium under investigation using the above-described calculations.

DETAILED DESCRIPTION OF THE INVENTION

The problem addressed by the present invention is how to produce an oscillatory stress throughout the region to be imaged so that the strain can be measured using MR elastography. In addition, the mechanical properties of the tissues that are most analogous to palpation can be determined from the measured strain only if the strain is produced by an oscillatory shear stress rather than a compressive or tensile stress. However, structures such as the brain are surrounded by bone or other rigid materials that impede direct application of shear stress to the surface of the structure of interest.

The discovery of the present invention is that a shear stress need not be applied directly to the subject to produce the desired strain waves deep inside the subject. Instead, the entire region of interest, or object can be shaken in an oscillatory motion, and the inertia of the moving tissues will produce forces throughout the subject. These forces produce stain through the subject that can be effectively detected with MR elastography. The inertial forces establish oscillations at the driven frequency, and mechanical shear waves propagate throughout the tissue. The shear wave front orientation is generalized within the subject, and can lead to local minima and maxima. Local wave fronts required for analysis of mechanical properties are produced.

The time delay or phase offset between the mechanical oscillation and the MR imaging encoding gradients is adjusted between several image acquisitions in order to provide images of the mechanical shear waves at different phases of propagation. These images are then processed to estimate the local frequency within each pixel. This estimation is ultimately used to determine tissue elasticity/compressibility as discussed above and in U.S. Pat. No. 5,592,085.

Referring particularly to FIG. 1, the preferred embodiment of the invention is used for imaging the brain of a human subject. The patient's head is placed in a head coil 10 such as that disclosed in U.S. Pat. No. 5,185,576 entitled "Local Gradient Coil" which is incorporated herein by reference. The head coil 10 contains an rf coil (not shown) which receives the NMR signals produced during the scan and one or more sets of local gradient coils (not shown) which produce magnetic field gradients during the scan to spatially resolve the source of the NMR signals. The patient's brain is encircled by the head coil 10, but a series of openings 12 are provided in the head coil 10 below the brain and in substantial alignment with the patient's mouth.

The MRE transducer 14 of the present invention is mounted on top of the head coil 10 and it extends downward through an opening 12 into the patient's mouth. The transducer 14 includes a support bar 16 which is securely fastened to the head coil 10 and provides a pivot point 18 aligned directly over the patient's mouth. A drive shaft 20 is rotatably fastened at the pivot point 18 and it extends upward therefrom to fasten to a drive coil 22. The drive coil 22 is comprised of a coil of wire wound around the substantially vertical axis of the drive shaft 20. The coil has an area of approximately $3 \times 10^{-4}$ meters squared and is comprised of 200 turns of 30 Awg copper wire. Leads 24 connect the coil 22 to a source of alternating current as discussed above and described in more detail in the above-cited U.S. Pat. No. 5,592,085 which is incorporated herein by reference.

Referring still to FIG. 1, the polarizing magnetic field $B_0$ produced by the MRI system is directed along the axes of the head coil 10 and perpendicular to the axis of the drive coil 22. In the preferred embodiment a field of 1.5 Tesla is employed. When an alternating current is applied to the drive coil 22, the interaction of its magnetic field with the polarizing field $B_0$ produces a force which rotates the drive shaft 20 back and forth about the pivot point 18.

Figure 2:
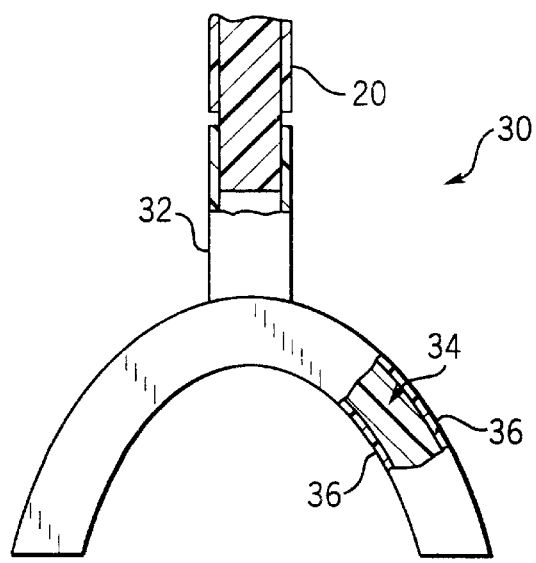
FIG. 2 is a front view with part cut away of a bite block which forms part of the transducer of FIG. 1.
Figure 3:
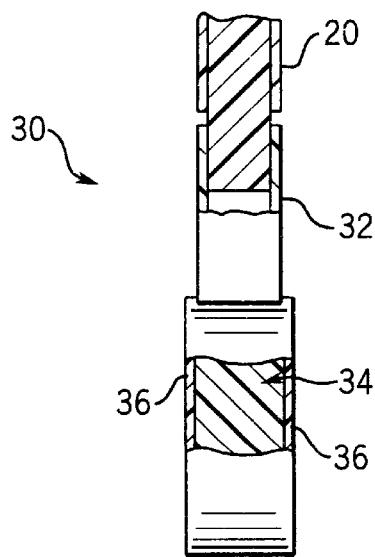
FIG. 3 is a side view with parts cut away of the bite block of FIG. 2.

Connected to the lower end of the drive shaft 20 and extending downward into the user's mouth is a bite block 30. As shown best in FIG. 2, the bite block 30 has a wye shape with its stem 32 extending upward to connect to the drive shaft 20. This stem 32 is a hollow tube which is bonded to a unshaped member 34. The upper end of the stem 32 slides over the lower end of the drive shaft 20 which is shaped to provide a friction fit with the inner surface of the tubular stem 32. A set of bite blocks 30 of differing sizes and shapes may thus be easily interchanged to properly fit the patient.

Both the stem 32 and the unshaped member 34 are formed from a non-ferromagnetic material. An acrylic polymer is employed in the preferred embodiment. To provide a better surface for transferring the movement of the bite block 30 to the teeth of the patient, the u-shaped member 34 is coated with a compliant material indicated at 36. A resin sold under the trademark "Teflon" is employed in the preferred embodiment, and it coats the surfaces to a thickness of one quarter inch.

When an alternating current is applied to the drive coil 22, the bite block 30 is moved back and forth in the direction indicated by arrow 40. Because the patient's head pivots about the neck, this oscillatory motion causes the brain to move up and down, as indicated by arrow 42. The inertial forces generated by this motion produces strain waves throughout the brain which may be detected using the MR elastography method. Frequencies in the range of 100 Hertz have provided the best results. The magnitude of the motion is approximately 50 micrometers. This motion is sufficient for magnetic resonance elastography, but it is too small to be sensed by the patient.

Figure 4:
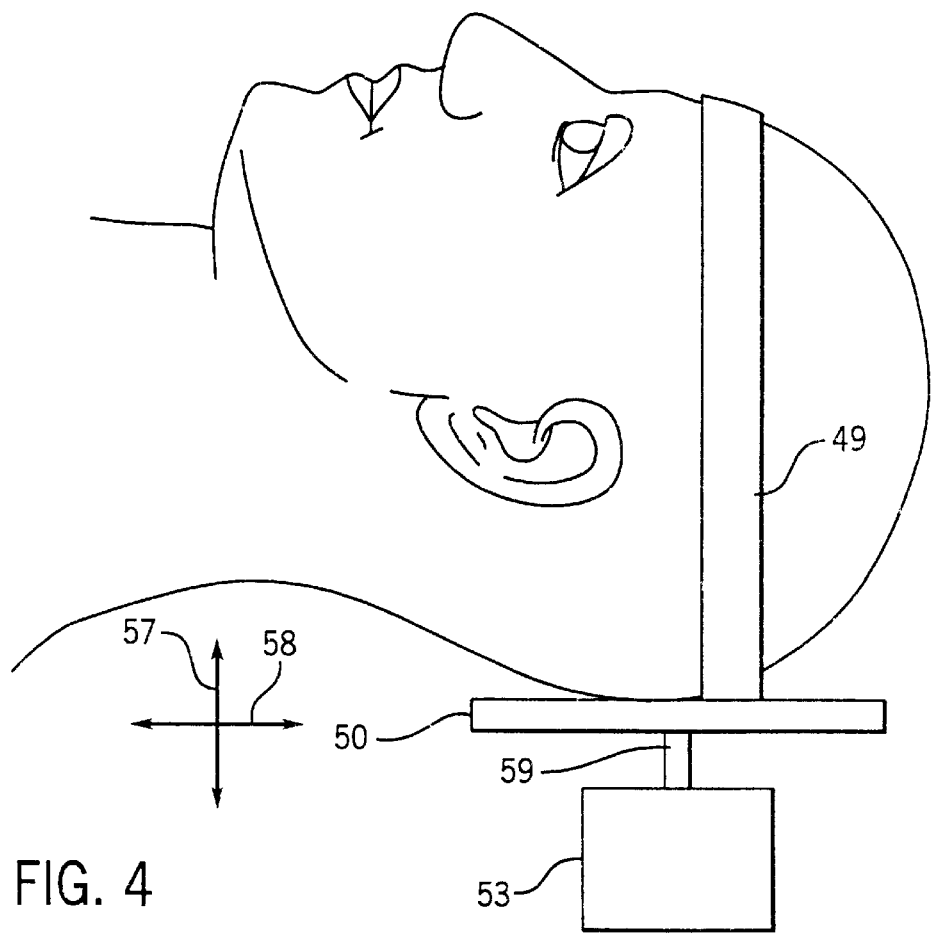
FIG. 4 is an elevation view of a second embodiment.
Figure 5:
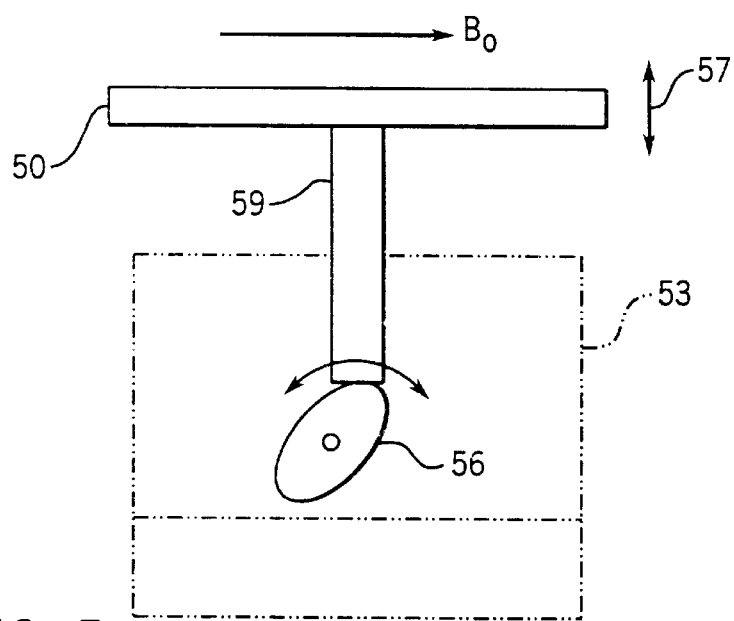
FIG. 5 is a side elevation view of another transducer used to practice the invention.
Figure 6:
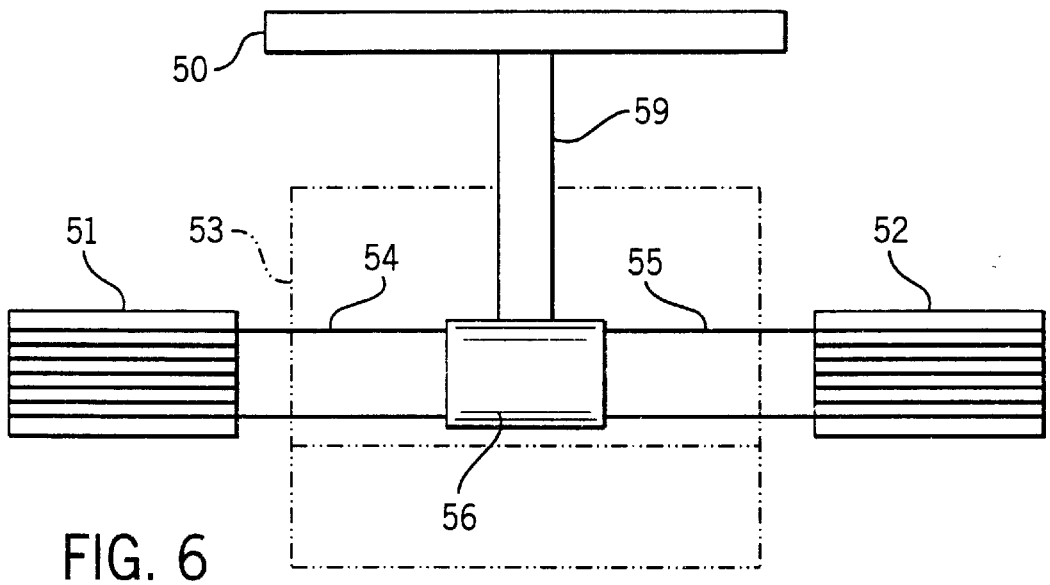
FIG. 6 is a front elevation view of the device shown in FIG. 5.
Figure 7:
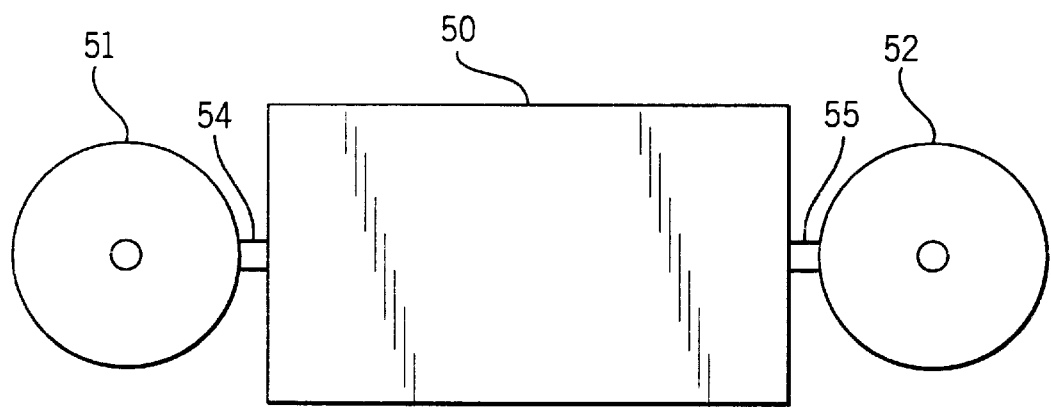
FIG. 7 is a top plan view of the device shown in FIG. 5.
Figure 8:
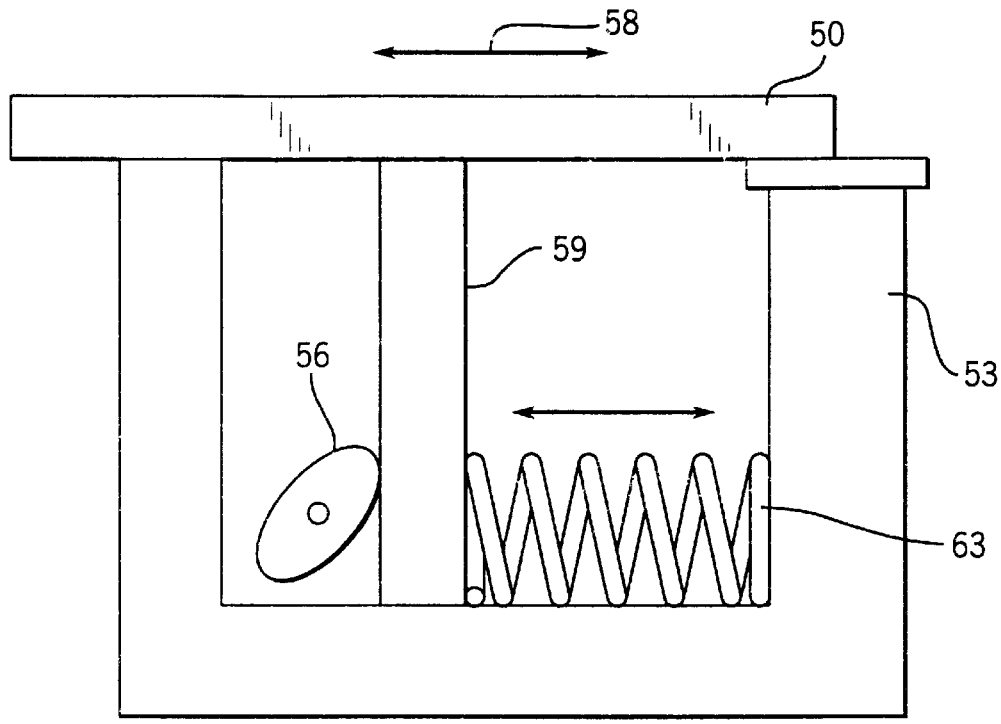
FIG. 8 is a view similar to FIG. 5 showing still another transducer.

Referring to FIGS. 4–8, a second embodiment tightly couples a human head to a vibrating platform 50 by a strap 49. The platform 50 is vibrated in the Y or Z direction shown by arrows 57 and 58, respectively, by drive coils 51 and 52 disposed in housing 53 connected to cam 56. As seen in FIGS. 5–7, drive coils 51 and 52 are connected to shafts 54 and 55 and oscillate cam 56. This provides vibration in the Y direction. Referring specifically to FIG. 8, alternatively the cam 56 can be positioned at the side of drive shaft 59 with a spring 63 positioned at the opposite side to effect a vibration in the Z direction as shown by arrow 58. These oscillatory motions of the platform 50 coupled to skull causes the brain to move along directions Y or Z.

Figure 9:
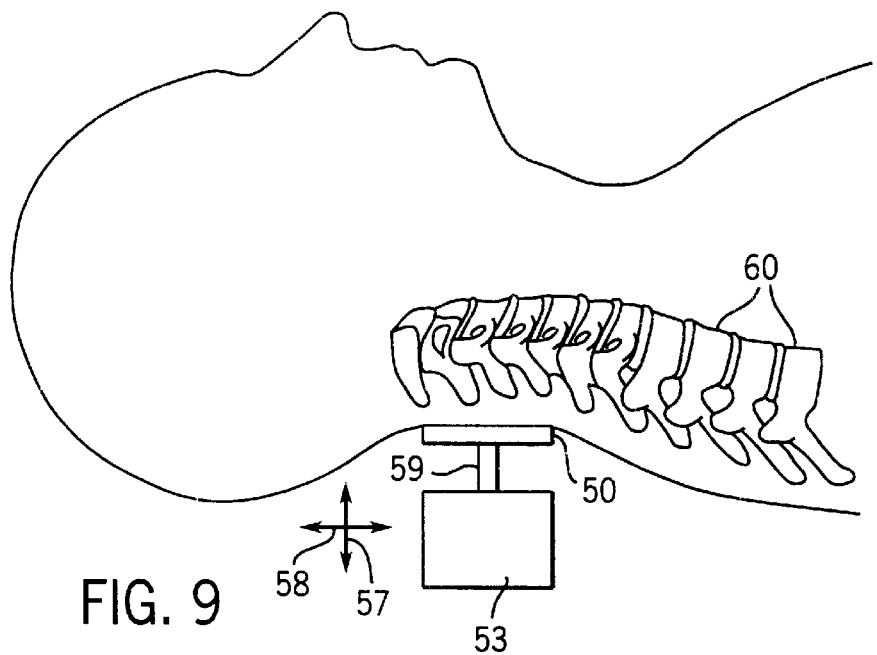
FIG. 9 is a elevation view of a third embodiment.

FIG. 9 depicts a third embodiment similar to FIG. 4 except the oscillatory motion is applied to the spinal cord, and the coupling means includes the vertebrae 60 which surround it. The same vibrating platform 50 is employed as previously described in conjunction with the embodiment of FIG. 4 which is vibrated in the direction of arrows 57 and 58.

We claim:

1. A device for applying an oscillatory stress throughout an object positioned in the polarizing magnetic field of an NMR imaging system, the combination comprising:

a driver having a pair of connections to a source of oscillating electric current and being responsive to the electric current to provide an oscillatory motion, the driver including a coil of wire which interacts with the polarizing magnetic field to produce the oscillatory motion; and coupling means for engaging the object and connected to the driver for imparting an oscillatory motion to the object, said driver providing a mechanical contact with the coupling means;

wherein the oscillatory motion imparted to the object produces oscillatory stress throughout the object which enables an MR elastographic image to be acquired.

2. A device for applying an oscillatory stress to the human brain positioned in the polarizing magnetic field of an NMR imaging system, the combination comprising:

a driver having a pair of connections to a source of oscillating electric current and being responsive to the electric current to provide an oscillatory motion; and coupling means including the skull surrounding the brain and connected to the driver for imparting an oscillatory motion to the brain;

wherein the oscillatory motion imparted to the brain produces oscillatory stress to the brain which enables an MR elastographic image to be acquired.

3. A device for applying an oscillatory stress to the teeth of a human positioned in the polarizing magnetic field of an NMR imaging system, the combination comprising:

a driver having a pair of connections to a source of oscillating electric current and being responsive to the electric current to provide an oscillatory motion; and coupling means including a bite block for engaging the teeth and connected to the driver for imparting an oscillatory motion to the teeth;

wherein the oscillatory motion imparted to the teeth produces oscillatory stress to the teeth which enables an MR elastographic image to be acquired.

4. A device for applying an oscillatory stress to the human spinal cord positioned in the polarizing magnetic field of an NMR imaging system, the combination comprising:

a driver having a pair of connections to a source of oscillating electric current and being responsive to the electric current to provide an oscillatory motion; and coupling means including the vertebrae which surround the spinal cord for imparting an oscillatory motion to the spinal cord;

wherein the oscillatory motion imparted to the spinal cord produces oscillatory stress to the spinal cord which enables an MR elastographic image to be acquired.

5. A device for applying an oscillatory stress to the human spinal cord positioned in the polarizing magnetic field of an NMR imaging system, the combination comprising:

a driver having a pair of connections to a source of oscillating electric current and being responsive to the electric current to provide an oscillatory motion; and coupling means including a platform constructed and arranged to contact vertebrae which surround the spinal cord and connected to the driver for imparting an oscillatory motion to the spinal cord;

wherein the oscillatory motion imparted to the spinal cord produces oscillatory stress to the spinal cord which enables an MR elastographic image to be acquired.

* * * * *